United States Patent [19]

Pawlowski et al.

[11] Patent Number: 5,346,806
[45] Date of Patent: Sep. 13, 1994

[54] ACID-CLEAVABLE RADIATION-SENSITIVE COMPOUNDS, RADIATION-SENSITIVE MIXTURE CONTAINING THESE COMPOUNDS, AND RADIATION-SENSITIVE RECORDING MATERIAL PRODUCED WITH THIS MIXTURE

[75] Inventors: Georg Pawlowski, Wiesbaden, Fed. Rep. of Germany; Ralph Dammel, Coventry, R.I.; Horst Roeschert, Ober-Hilbersheim, Fed. Rep. of Germany; Walter Spiess, Dieburg, Fed. Rep. of Germany; Charlotte Eckes, Mainz, Fed. Rep. of Germany

[73] Assignee: Hoechst Aktiengesellschaft, Frankfurt am Main, Fed. Rep. of Germany

[21] Appl. No.: 871,011

[22] Filed: Apr. 20, 1992

[30] Foreign Application Priority Data

Apr. 20, 1991 [DE] Fed. Rep. of Germany ....... 4112969

[51] Int. Cl.$^5$ ............... G03C 1/73; G03C 1/725; G03F 7/025; G03F 7/027
[52] U.S. Cl. .................................. 430/284; 430/176; 430/270; 430/286; 430/292; 430/300; 430/302; 430/323; 430/326; 430/914; 430/919; 430/925
[58] Field of Search ............... 430/284, 270, 286, 170, 430/292, 300, 302, 323, 914, 919, 925, 326

[56] References Cited

U.S. PATENT DOCUMENTS 4,101,323  7/1978  Buhr et al. ............................. 96/35
4,247,611  1/1981  Sander et al. ....................... 430/286
4,883,740  11/1989 Schwalm et al. ................... 430/270

OTHER PUBLICATIONS

Reichmanis et al., "Chemistry and Processes for Deep-UV Resists," *Microelectronic Engineering*, vol. 13, pp. 3–10 (Mar. 1991).

(List continued on next page.)

*Primary Examiner*—John Kight, III
*Assistant Examiner*—P. Hampton-Hightower
*Attorney, Agent, or Firm*—Foley & Lardner

[57] ABSTRACT

Ligomeric sulfonic acid derivatives having repeating units of the formula I

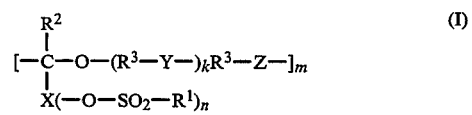

in which
  $R^1$ is an alkyl, haloalkyl or aryl radical,
  $R^2$ is a hydrogen atom, an alkyl, alkenyl or aryl radical or the group $(R^1-SO_2-O-)_nX-$,
  $R^3$ is a cycloalkylenedialkyl, cycloalkenylenedialkyl, arylenedialkyl, heteroarylenedialkyl group, alkylene, alkenylene, alkynylene, cycloalkylene or arylene group,
  X is an alkylene, cycloalkylene or arylene group Y is O, S, CO, CO—O, $SO_2$, $SO_2$—O, $NR^4$, CO—NH, O—CO—$NR^5$, NH—CO—$NR^5$ or $NR^5$—CO—O,
  Z is O, CO—$NR^6$, O—CO—$NR^6$ or NH—CO—$NR^6$,
  $R^4$ is an acyl radical,
  $R^5$ is a hydrogen atom or an alkyl-, cycloalkyl, alkenyl, alkynyl or aryl radical,
  $R^6$ is an alkyl, cycloalkyl, alkenyl, alkynyl or aryl radical,
  k is 0, 1, 2, 3 or 4,
  m is an integer greater than 1 and
  n is 1, 2 or 3, generate sulfonic acids under irradiation and are cleavable by the latter. In combination with alkali-soluble binders, they give positive-working mixtures which are used especially in recording materials for UV radiation and high-energy radiation. The recording materials are distinguished by a high resolution in conjunction with high image contrast and excellent storage stability.

20 Claims, No Drawings

OTHER PUBLICATIONS

Schlegel et al., "Highly Sensitive Positive Deep UV Resist Utilizing a Sulfonate Acid Generator and a Tetrahydropyranyl Inhibitor," *Microelectronic Engineering*, vol. 13, pp. 33–36 (Mar. 1991).

CA 116(24):245275k, "Positive Working Radiation Sensitive Composition and Radiation-Sensitive Recording Material for Exposure Using UV-Radiation," Roeschert et al, Jun. 15, 1992.

C. Wilson, et al, "Introduction to Microlithography, Organic Resist Materials–Theory and Chemistry", ACS Symposium Series 219, 87, Mar. 20–25, 1983, pp. 88–159.

C. Petropoulos, "Synthesis of Novel Photodegradable Poly(o–Nitrobenzaldehyde Acetal) Polymers", J. Polym. Sci., Polym. Chem. Ed., 15, 1977, pp. 1637–1644.

F. M. Houlihan, et al, "An Evaluation of Nitrobenzyl Ester Chemistry for Chemical Amplification Resists", SPIE, vol. 920, 1988, pp. 67–74.

ACID-CLEAVABLE RADIATION-SENSITIVE COMPOUNDS, RADIATION-SENSITIVE MIXTURE CONTAINING THESE COMPOUNDS, AND RADIATION-SENSITIVE RECORDING MATERIAL PRODUCED WITH THIS MIXTURE

BACKGROUND OF THE INVENTION

1. Field of the Invention

The invention relates to radiation-sensitive and acid-cleavable compounds and to a radiation-sensitive mixture which is positive-working, i.e., which becomes soluble as a result of irradiation, which contains these compounds. The mixture contains (a) a binder which is insoluble in water and soluble or at least swellable in aqueous alkaline solutions, and
(b) an oligomeric compound which generates a strong acid under the action of actinic radiation and which has at least one acid-clearable C—O—C bond.

The invention also relates to a radiation-sensitive recording material produced from this mixture which is suitable for producing photoresists, electronic components, printing plates or for chemical milling.

2. Description of Related Art

The continuing reduction in the size of the structures, for example, in chip manufacture down into the range of less than 1 $\mu$m, requires modified lithographic techniques. To form images of such fine structures, radiation of a short wavelength is used, such as high-energy LrV light, electron beams and X-rays. The radiation-sensitive mixture must be adapted to the short-wave radiation. A compilation of the requirements to be met by the radiation-sensitive mixture is given in the article by C. G. Willson "Organic Resist Materials—Theory and Chemistry" [Introduction to Microlithography, Theory, Materials, and Processing, editors L. F. Thompson, C. G. Willson, M. J. Bowden, ACS Symp. Ser., 219, 87 (1983), American Chemical Society, Washington].

There is therefore an increased demand for radiation-sensitive mixtures which can be used in the more recent technologies, such as mid-UV or deep-UV lithography [exposure, for example, with excimer lasers at wavelengths of 305 nm (XeF), 248 nm (KrF), 193 nm (ArF)], electron beam lithography or X-ray lithography, and which, furthermore, are preferably sensitive in a wide spectral range and correspondingly can also be used in conventional UV lithography.

Positive-working radiation-sensitive mixtures for producing radiation-sensitive recording materials are known. Mixtures which contain o-quinone--diazide derivatives in binders soluble in aqueous alkaline media, for example novolaks or polyhydroxystyrenes, are commercially available. However, the sensitivity of these materials to actinic radiation, and especially high-energy short-wave radiation, such as light from a KrF-excimer laser having a wavelength of 248 nm or electron beams, is inadequate.

Positive-working radiation-sensitive mixtures are also known in which an acid is generated by the action of actinic radiation on a photoinitiator contained in this mixture and this acid then, in a subsequent reaction, renders an acid-cleavable compound likewise contained in the mixture soluble in the irradiated areas under the action of an appropriate, preferably aqueous alkaline developer. Such materials are in general distinguished by an enhanced sensitivity to actinic radiation.

Numerous mixtures are known which contain, as the essential components, a polymeric binder soluble in aqueous alkaline solutions, a solubility-inhibiting compound and a compound which, on irradiation, generates the acid required for cleavage. The binder is in most cases a novolak resin. Many of these mixtures have a high sensitivity to actinic radiation. They are designated as chemically amplified, photocatalytic 3-component systems.

Of these mixtures, those whose acid-clearable component contains one or more acetal units have gained commercial importance. These mixtures have, however, certain disadvantages. They possess only a limited stability on the substrate materials to which they have to be applied, which leads to an unsatisfactory, not reducible reproduction of the image original. This can be improved only by introducing additional protective layers, for example according to DE-A 3,621,376, equivalent to U.S. Pat. No. 4,840,867. The causes of the deterioration in the image reproduction are not fully known and have not been adequately investigated. For example, the process window, i.e., the processing latitude, for the exposure of these mixtures is very narrow and frequently not unambiguously reproducible. In particular, the quality of the image reproduction greatly depends on the time difference between exposure and development, the so-called delay time. In principle, it must be assumed that diffusion processes which cause this behavior are not easily controllable. In addition, however, it may be presumed that, during drying of the mixture on a substrate material, partial vaporization of the photoinitiator or of the acid-unstable compound or segregation of the individual mixture constituents takes place, which is observed with particular frequency in the case of acid-unstable compounds having a low solubility in the usual coating solvents.

It is also known from the papers by C. C. Petropoulos [J. Polym. Sci., Polym. Chem. Ed., 15, 1637 (1977)] that aromatic acetals which carry a nitro group in the vicinal position, are photodecomposable by high-energy UV radiation without acid catalysis, and can be used in positive-working radiation-sensitive recording materials. The photosensitivity of these compounds is likewise inadequate for applications in practice, since their photoreaction cannot be chemically amplified.

In DE-A 3,721,741, equivalent to U.S. Pat. No. 4,883,740, radiation-sensitive mixtures are described which contain a polymeric binder insoluble in water and soluble in aqueous alkaline solutions, and an organic compound which contains at least one acid-cleavable grouping and a grouping which generates a strong acid under the action of radiation. The radiation-sensitive groups described are exclusively onium salt groups, in particular sulfonium salt groups.

The use of onium salts, such as diazonium, phosphonium, sulfonium and iodonium salts, of nonnucleophilic acids such as $HSbF_6$, $HAsF_6$ or $HPF_6$ as photolytic acid generators involves disadvantages which drastically restrict their possible uses in various fields of application. For example, many of the onium salts are toxic. Their solubility is inadequate in many solvents, which is why only a few solvents are suitable for preparing a coating solution. Furthermore, when the onium salts are used, undesired foreign atoms are sometimes introduced which can cause interference with the process, especially in microlithography. Moreover, the onium salts form Brönstedt acids, which have a very severe corrosive action, in the photolysis. These acids attack sensitive substrates, so that the use of such mixtures leads to unsatisfactory results. Halogen compounds such as trichloromethyltriazine derivatives or trichloromethyloxadiazole derivatives also form hydrohalic acids which have a severely corrosive action.

In more recent papers by F. M. Houlihan et al., SPIE 920, 67 (1988), it was shown by reference to positive-working systems that, in addition to the above-mentioned acid generators, nitrobenzyl tosylates, which on exposure generate sulfonic acids having a low migration tendency, can be used in certain acid-unstable resist formulations. It can be deduced from these results that such compounds can also be used for photo-curable systems. However, the sensitivities thus achieved, especially to UV radiation from 350 to 450 nm, and the thermal stability of the photoresists have proven to be inadequate.

Because of the inadequacies and disadvantages described above, there is a demand for radiation-sensitive mixtures which do not have these disadvantages and possess a reactivity suitable in practice.

SUMMARY OF THE INVENTION

It was therefore an object of the invention to provide photolytically acid-generating and acid-clearable compounds, and a radiation-sensitive mixture based thereon, where the photolytically acid-generating compound should be as stable as possible on all known substrates and gives an acid as the photolysis product, which does not have a corrosive action. Furthermore, the invention should provide a radiation-sensitive mixture which, in particular, avoids a segregation of the photoactive compound and of the solubility-differentiating compound.

It was also an object of the present invention to provide a radiation-sensitive mixture which has high sensitivities over a wide spectral range, and which is suitable for irradiation with high-energy UV radiation.

It was further an object of the present invention to provide a recording material which provides a defect-free image of the mask having high flank stability, and which is suitable for use in the production of photoresists, electronic components, and printed plates.

It is also an object of the present invention to provide a process for producing such a recording material.

It was also an object to provide a method of preparing an image pattern by use of the recording materials.

In accomplishing the foregoing objectives, there has been provided, in accordance with one aspect of the present invention, an oligomeric compound which generates a strong acid under the action of actinic radiation and which has at least one acid-clearable C—O—C bond, having repeating units of the formula

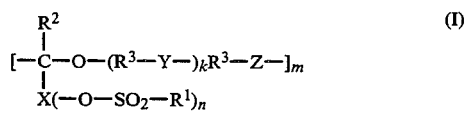

in which
R$^1$ is an alkyl, haloalkyl or aryl radical,
R$^2$ is a hydrogen atom, an alkyl, alkenyl or aryl radical or the group (R$^1$—SO$_2$—O—)$_n$X—,
R$^3$ is a cycloalkylenedialkyl, cycloalkenylenedialkyl, arylenedialkyl, heteroarylenedialkyl, alkylene, alkenylene, alkynylene, cycloalkylene or arylene group, X is an alkylene, cycloalkylene or arylene group if n is 1, or a (n+1)—valent radical of an alkene, cycloalkene, or arene if n is 2 or 3.
Y is O, S, CO, CO—O, SO$_2$, SO$_2$—O, NR$^4$, CO—NH, O—CO—NR$^5$, NH—CO—NR$^5$ or NR$^5$—CO—O,
Z is O, CO—NR$^6$, O—CO—NR$^6$ or NH—CO—NR$^6$,
R$^4$ is an acyl radical,
R$^5$ is a hydrogen atom or an alkyl, cycloalkyl, alkenyl, alkynyl or aryl radical,
R$^6$ is an alkyl, cycloalkyl, alkenyl, alkynyl or aryl radical,
k is an integer from 0, 1, 2, 3 or 4,
m is an integer greater than 1 and n is an integer from 1, 2 or 3,
where R$^3$ and Y in recurring groupings (R$^3$—Y—) can have identical or different definitions.

If m or n or both are greater than 1, the X, Y and R groups are the same or different in each repeating unit.

There has further been provided a positive-working radiation-sensitive mixture comprising this compound and at least one binder which is insoluble in water and soluble or at least swellable in aqueous alkaline solutions.

There has further been provided a positive-working radiation sensitive recording material comprising a support and a radiation-sensitive layer, wherein the layer comprises a radiation-curable mixture as described above.

There has also been provided a method of producing such a recording material which comprises dissolving the radiation sensitive mixture in a solvent, applying the resultant solution to the support, and removing the solvent.

There has further been provided a method of preparing an image pattern comprising irradiating the radiation-sensitive layer of the recording material imagewise, optionally heating the layer, treating the layer with a developer which removes the irradiated areas of the layer, and optionally post-hardening the developed layer structures.

Further objects, features, and advantages of the present invention will become apparent from the detailed description of preferred embodiments that follows.

DETAILED DESCRIPTION OF THE PREFERRED EMBODIMENTS

Those compounds of the formula I are preferred in which R$^1$ is an alkyl radical having 1 to 6 carbon atoms, which may be halogenated, in particular highly fluorinated, i.e., in which at least 50 % of the hydrogen atoms are replaced by fluorine atoms, or an aryl radical having 6 to 12 carbon atoms, in particular a mononuclear aryl radical. The aryl radical may optionally carry 1 to substituents, in particular, one or more of halogen atoms, nitro groups, cyano groups or alkyl or alkoxy groups having 1 to 3 carbon atoms.

R$^2$ is preferably a hydrogen atom, an alkyl radical having 1 to 6 and especially 1 to 3 carbon atoms, an alkenyl radical having 2 to 6 and especially 2 to 4 carbon atoms or an aryl radical having 6 to 12 carbon atoms, which may be substituted by halogen atoms, alkyl radicals having 1 to 3 carbon atoms, alkanesulfonyloxy radicals having 1 to 5 carbon atoms or alkoxy radicals having 1 to 3 carbon atoms, or a radical of the formula (R$^1$—SO$_2$O)$_n$X. R$_2$ is particularly preferably a hydrogen atom.

R³ preferably is a cycloalkenylenedialkyl, cycloalkylenedialkyl, arylenedialkyl or heteroarylenedialkyl group, each preferably having 6 to 20 and especially 6 to 15 carbon atoms; an alkylene group having 1 to 8 carbon atoms, an alkenylene or alkynylene group having 2 to 10 and especially 2 to 6 carbon atoms, a cycloalkylene group having 4 to 12 carbon atoms or an arylene group having 6 to 10 carbon atoms, in particular a mononuclear arylene group having 6 to 8 carbon atoms.

X is preferably an alkylene group having 2 to 10 carbon atoms, more preferably 2 to 8 carbon atoms, a cycloalkylene group having 2 to 10 carbon atoms, more preferably 5 to 8 carbon atoms or an arylene group having 6 to 12 carbon atoms, in particular a mononuclear arylene group having 6 to 10 carbon atoms, arylene groups being particularly preferred. These groups are in each case substituted by 1 to 3 sulfonyloxy groups $R^1$-$SO_2$—O—.

Y preferably is O, S, $NR^4$, $SO_2$, O—CO—$NR^5$ CO—O NH—CO—$NR^5$ or $NR^5$—CO—O.

In the cases where k is greater than 1, the groups $R^3$ and Y can have the same or a different definition in each recurring unit.

$R^4$ preferably is an alkanoyl radical having 2 to 6 carbon atoms or an aroyl radical having 7 to 10 carbon atoms. It can also be the radical of a different acid, for example, a sulfonyl or phosphonyl radical. Aroyl radicals are particularly preferred.

$R^5$ preferably is a hydrogen atom, an alkyl radical having 1 to 8 and especially 1 to 5 carbon atoms, an alkenyl or alkynyl radical having 2 to 6 carbon atoms or an aryl radical having 6 to 10 and especially 6 to 8 carbon atoms.

$R^6$ preferably is an alkyl radical having 1 to 8 and especially 1 to 5 carbon atoms, an alkenyl or alkynyl radical having 2 to 6 carbon atoms or an aryl radical having 6 to 10 and especially 6 to 8 carbon atoms.

m preferably is an integer greater than 3 and more preferably between 4 and 40.

Those compounds of the formula I are particularly preferred in which $R^1$ is a methyl, ethyl, trifluoromethyl or 1,1,2,3,3,3-hexafluoropropyl radical or a phenyl radical which may be substituted by 1 to 3 alkyl or alkoxy groups having 1 to 3 carbon atoms, 1 to 3 halogen atoms, 1 or 2 nitro, cyano or trifluoromethyl groups or appropriate combinations thereof.

The termini of the oligomers bear H, OH or other groups, according to their methods of synthesis.

Any known method can be used to prepare the compounds according to the invention. This can be carried out, for example, analogously to the synthesis instructions given in DE-A 2,610,842, where the appropriate sulfonic acid ester derivative must be prepared in a preceding stage. The synthesis of typical and preferred representatives of these classes of compounds is described below by reference to individual examples.

PREPARATION EXAMPLE 1

1st stage: 80.6 g (0.66 mol) of 4-hydroxybenzaldehyde were dissolved in 200 ml of tetrahydrofuran, 138 ml of triethylamine were added and the mixture was cooled to −5° C. 125.8 g (0.66 mol) of p-toluenesulfonic acid chloride, dissolved in 330 ml of tetrahydrofuran and precooled to −5° C., were added dropwise to the above mixture at −8° to −5° C. Stirring was continued for 1 hour at room temperature. The solution was poured into 1,000 ml of distilled water, and the mixture was adjusted to pH 2 with concentrated hydrochloric acid. The oil which had precipitated was taken up in ether, and the aqueous phase was extracted with ether. The combined organic phases were washed with water and dried. After concentrating, a residue remained which was recrystallized from cyclohexane/methylene chloride. This gave 120 g (66.1%) of 4-(toluene-4sulfonyloxy)benzaldehyde (white solid having a melting point of 70° to 72° C.).

2nd stage: 7.2 g (0,026 mol) of 4-(toluene-4-sulfonyloxy)-benzaldehyde were heated under reflux together with 2.4 g (0,026 mol) of butane-1,4-diol, 4.25 g (0.0286 mol) of triethyl orthoformate and 100 mg of p-toluenesulfonic acid in 150 ml of toluene. After about 2 hours, a part of the distillate was taken off until the top temperature corresponded to the boiling point of pure toluene. This procedure was repeated until the top temperature no longer fell below the boiling point of pure toluene. After a further 2 hours, the distillation was assisted for about 45 minutes by applying a vacuum of 4 mm Hg, and all volatile constituents were distilled off. The cooled-down residue was taken up in methylene chloride, washed twice with 2% sodium hydroxide solution and deionized water each time, and the organic phase was dried. After removal of the solvent, 9.1 g of a yellow oil remained which proved to be the desired Compound 1 shown below on the basis of its NMR spectrum.

PREPARATION EXAMPLE 2

1st stage: 80.6 g (0.66 mol) of 3-hydroxybenzaldehyde were dissolved in 200 ml of tetrahydrofuran, 138 ml of triethylamine were added and the mixture was cooled to −5° C. 125.8 g (0.66 mol) of p-toluenesulfonic acid chloride, dissolved in 330 ml of tetrahydrofuran and precooled to −5° C., were added dropwise to the above mixture at −8° to −5° C. Stirring was continued for 1 hour at room temperature. The solution was poured into 1,000 ml of distilled water, and the mixture was adjusted to pH 2 with concentrated hydrochloric acid. The oil which had precipitated was taken up in ether, and the aqueous phase was extracted with ether. The combined organic phases were washed with water and dried. After concentrating, an oil remained which was recrystallized from cyclohexane. This gave 115 g (63.7%) of 3-(toluene-4-sulfonyloxy)-benzaldehyde (white solid having a melting point of 65° to 67° C.).

2nd stage: 7.2 g (0,026 mol) of 3-(toluene-4-sulfonyloxy)-benzaldehyde were heated in an oil bath to 130° C. together with 4.15 g (0,026 mol) of butyne-1,4diol, 4.25 g (0.0286 mol) of triethyl orthoformate and 100 mg of p-toluenesulfonic acid in 150 ml of toluene. After about 2 hours, a part of the distillate was taken off until the top temperature corresponded to the boiling point of pure toluene. This procedure was repeated until the top temperature no longer fell below the boiling point of pure toluene. After a further 2 hours, the distillation was assisted for about 45 minutes by applying a vacuum of 4 mm Hg, and all volatile constituents were distilled off. The cooled-down residue was taken up in methylene chloride, washed twice with 2% sodium hydroxide solution and deionized water each time, and the organic phase was dried. After removal of the solvent, 9.8 g of a dark, amber-colored melt remained which proved to be Compound 2 shown below.

PREPARATION EXAMPLE 3

1st stage: 8.29 g (0.06 mol) of 3,4-dihydroxy-benzaldehyde were dissolved in 40 ml of tetrahydrofuran, 18.5 ml of triethylamine were added, and the mixture cooled to −5° C. 22.9 g (0.12 mol) of p-toluenesulfonic acid chloride, dissolved in 80 ml of tetrahydrofuran and pre-cooled to −5° C., were added thereto dropwise at −8° to −5° C. Stirring was continued for 2 hours at room temperature. The solution was poured into 1,000 ml of distilled water, and the mixture was adjusted to pH 2 with concentrated hydrochloric acid. The oil which had precipitated solidified after prolonged stirring, to give a brown crystal paste. The crude product was filtered off with suction and dried. It was recrystallized from cyclohexane/methylene chloride with addition of active charcoal. This gave 15.9 g (59.4%) of 3,4-bis-(toluene-4-sulfonyloxy)-benzaldehyde (white solid having a melting point of 95° to 97° C.).

2nd stage: 11.6 g (0.026 mol) of 3,4-bis-(toluene-4-sulfonyloxy)-benzaldehyde were heated in an oil bath at 130° C. together with 3.75 g (0.026 mol) of triethylene glycol, 4.25 g (0.0286 mol) of triethyl orthoformate and 100 mg of p-toluenesulfonic acid in 150 ml of toluene. After about 2 hours, a part of the distillate was taken off until the top temperature corresponded to the boiling point of pure toluene. This procedure was repeated until the top temperature no longer fell below the boiling point of pure toluene. After a further 2 hours, the distillation was assisted for about 45 minutes by applying a vacuum of 4 mm Hg, and all volatile constituents were distilled off. The cooled-down residue was taken up in methylene chloride, washed twice with 2% sodium hydroxide solution and deionized water each time, and the organic phase was dried. After removal of the solvent, 13.8 g of a dark, honey-like liquid remained, which proved to be Compound 3 shown below.

PREPARATION EXAMPLE 4

7.2 g (0.026 mol) of 4-(toluene-4-sulfonyloxy)benzaldehyde (see Preparation Example 1, 1st stage) were heated under reflux in 150 ml of toluene together with 5.2 g (0.035 mol) of triethyl orthoformate and 8.82 g (0.06 mol) of a urethane alcohol prepared by reacting 1 mol of ethylene carbonate with 1 mol of n-propylamine, and 100 mg of p-toluenesulfonic acid. After about 2 hours, a part of the distillate was taken off until the top temperature corresponded to the boiling point of pure toluene. This procedure was repeated until the top temperature no longer fell below the boiling point of pure toluene. After a further 2 hours, the distillate was assisted for about 45 minutes by applying a vacuum of 4 mm Hg, and all volatile constituents were distilled off. The cooled-down residue was taken up in methylene chloride, washed twice with 2% sodium hydroxide solution and deionized water each time, and the organic phase was dried. After removal of the solvent, 10.8 g of a light-colored, viscous liquid remained which was subjected to a vacuum treatment at 180° C./0.01 mm Hg. In this treatment, a colorless liquid was stripped off. The remaining highly viscous residue proved to be Compound 4 shown below.

Further examples of compounds according to the invention are listed in the attached formulae 5 to 49. These compounds were synthesized analogously to known processes. Their structures were confirmed by elemental analysis and $^1$H-NMR Compound No. 1:

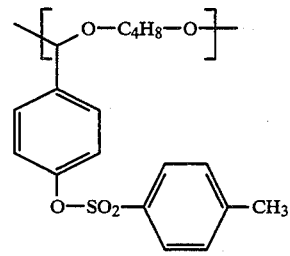

Compound No. 2

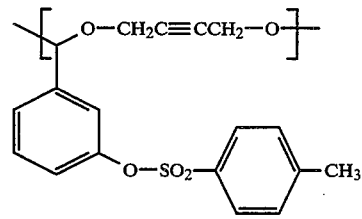

Compound No. 3

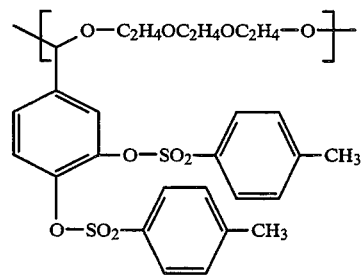

-continued
Compound No. 4
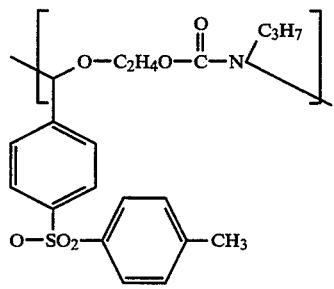
Compound No. 5
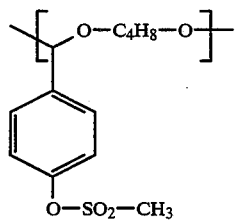
Compound No. 6
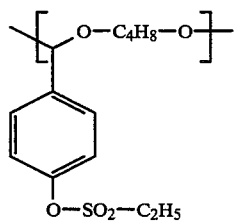
Compound No. 7
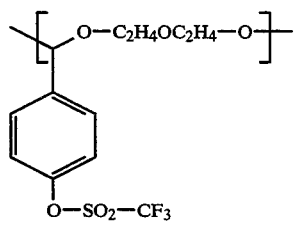
Compound No. 8
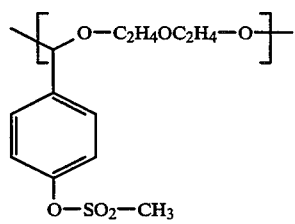
Compound No. 9
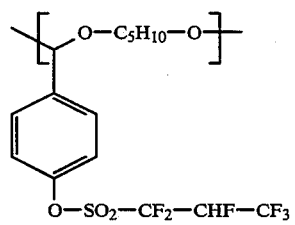
Compound No. 10

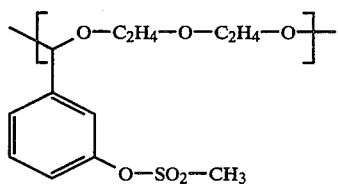
Compound No. 11
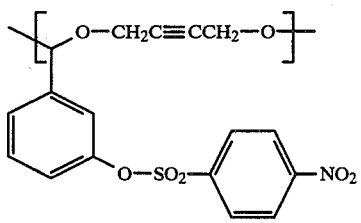
Compound No. 12
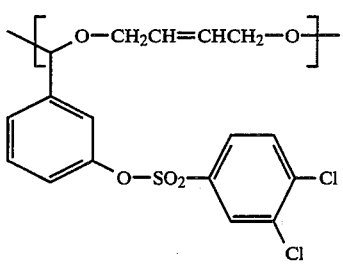
Compound No. 13
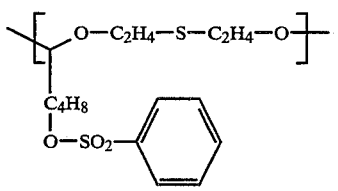
Compound No. 14
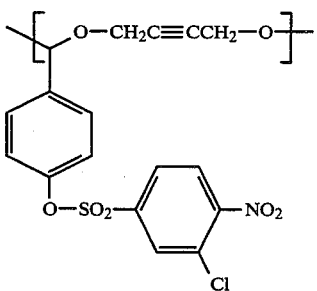
Compound No. 15
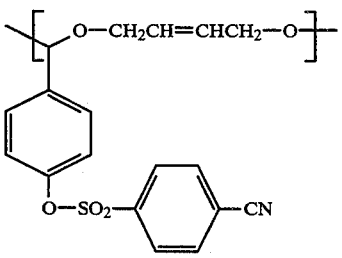
Compound No. 16

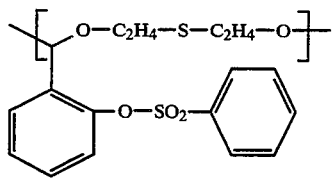
Compound No. 17
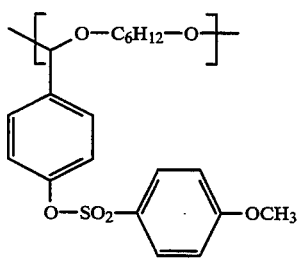
Compound No. 18
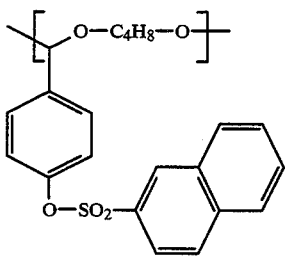
Compound No. 19
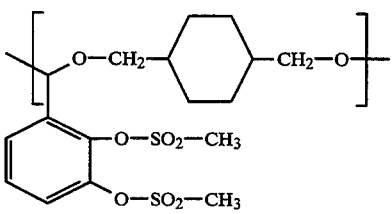
Compound No. 20
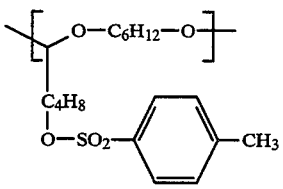
Compound No. 21
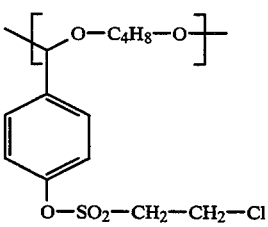
Compound No. 22

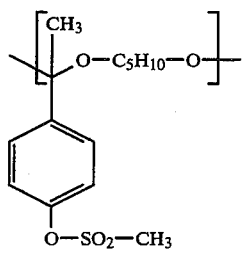
Compound No. 23
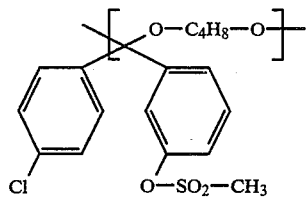
Compound No. 24
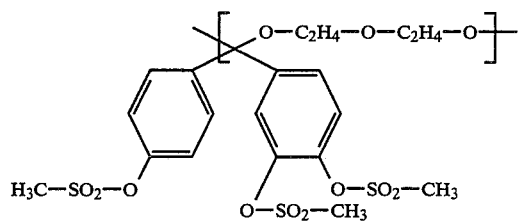
Compound No. 25
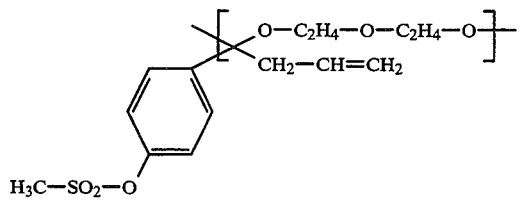
Compound No. 26
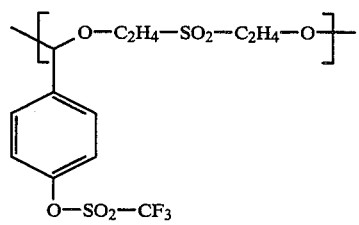
Compound No. 27
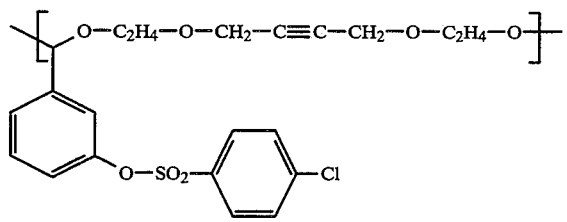
Compound No. 28

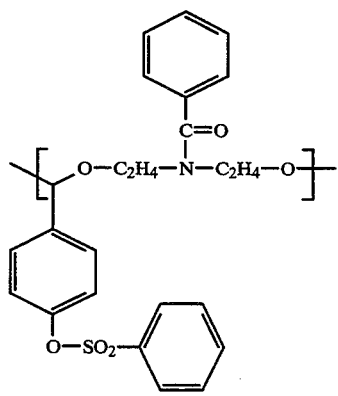
Compound No. 29
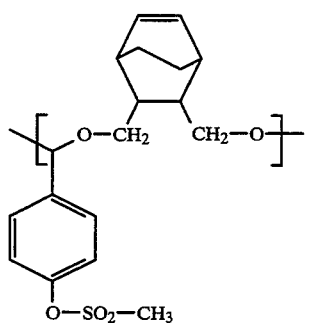
Compound No. 30
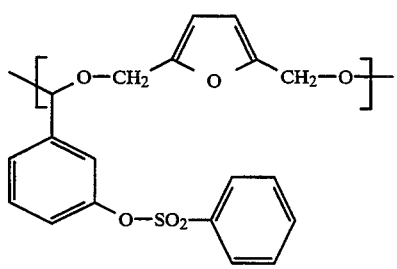
Compound No. 31
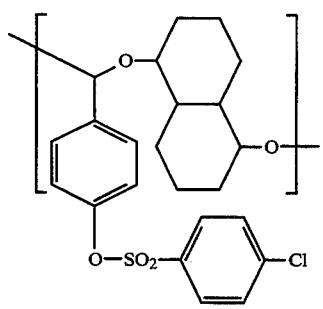
Compound No. 32

-continued
Compound No. 33
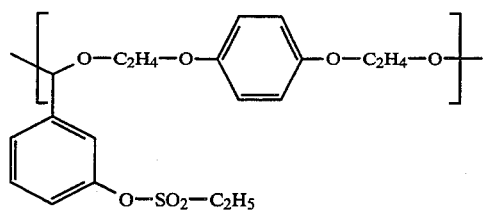
Compound No. 34
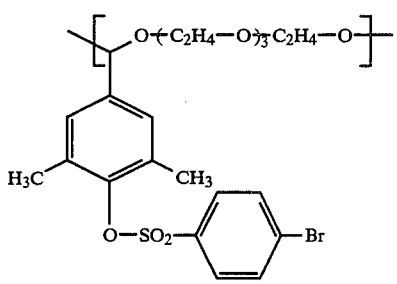
Compound No. 35
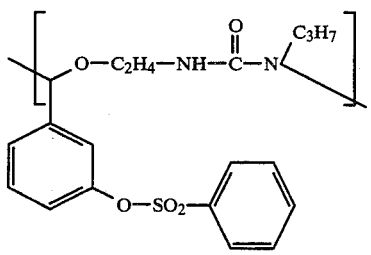
Compound No. 36
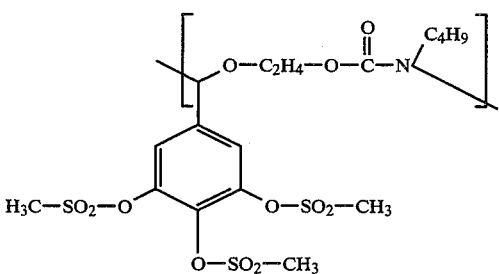
Compound No. 37
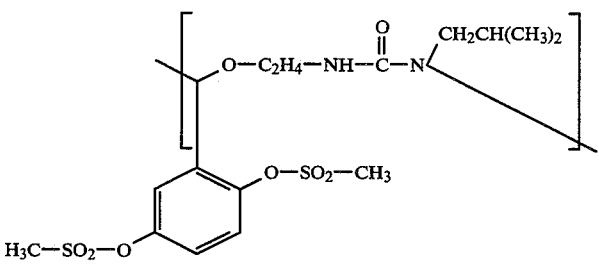
Compound No. 38

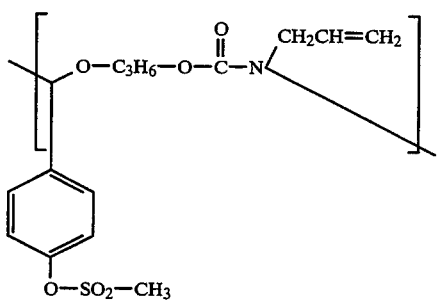
Compound No. 39
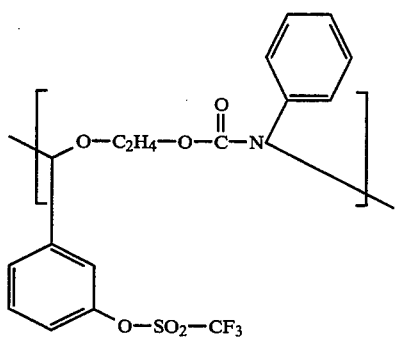
Compound No. 40
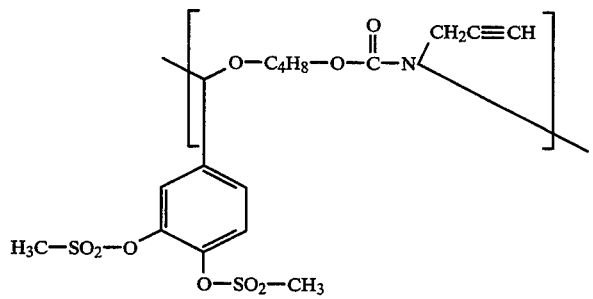
Compound No. 41
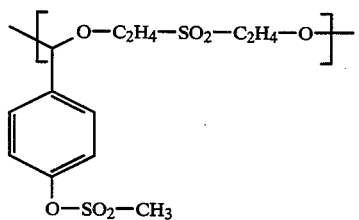
Compound No. 42
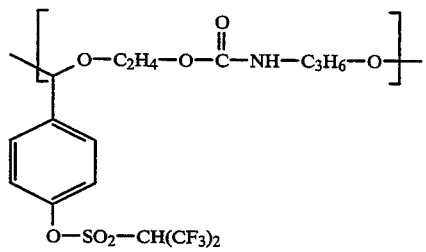
Compound No. 43

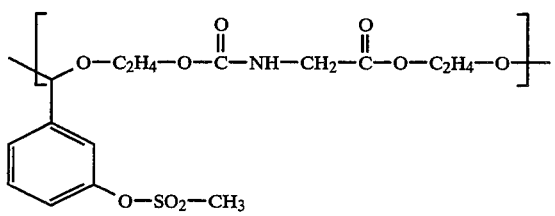
Compound No. 44
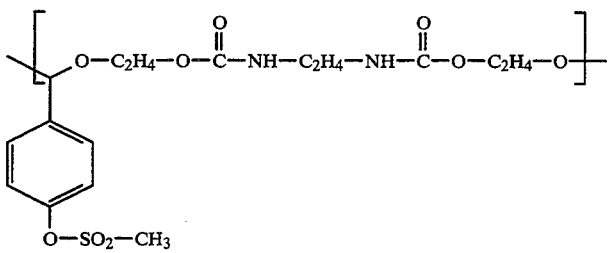
Compound No. 45
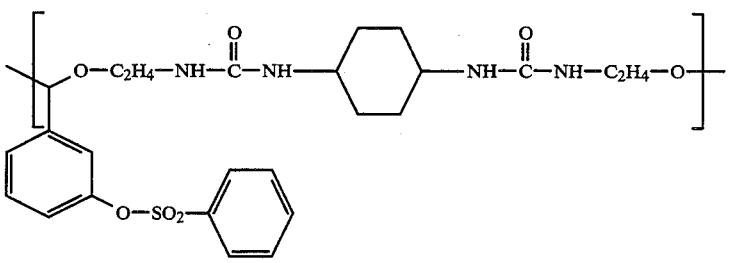
Compound No. 46
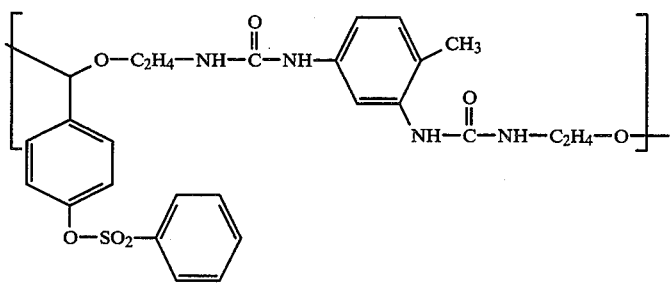
Compound No. 47
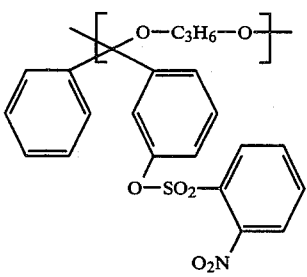
Compound No. 48
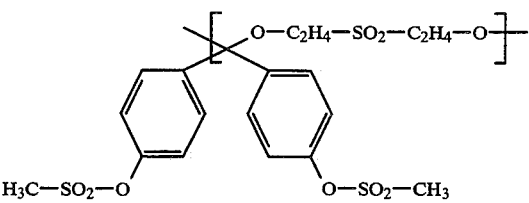
Compound No. 49

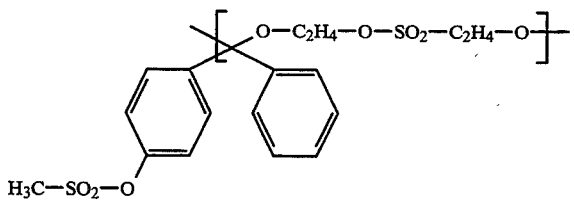

It is clear from the preparation methods that the resulting oligomeric compounds according to the invention of the formula I are formed by a condensation reaction. It is in the nature of such reactions that they form product mixtures which are composed of individual oligomers of different degrees of oligomerization, i.e. different values of "m". The use of the brackets in the above compounds indicates that the compounds may have varying values for "m." By means of a suitable polymer analysis, it was possible to prove that, as a result of optimized reaction control, more than 90% of the mixture has a degree of oligomerization of between 4 and 40, but monomeric, dimeric and trimeric compounds or compounds having a degree of oligomerization of >40 are also detectable in small quantities. The oligomer composition, that is, the value of m can, however, be made reproducible by using clearly fixed reaction conditions.

Those compounds of Formula I which have acetal structures are particularly preferred. This is to be ascribed to the fact that they are very readily accessible and, in addition, are also extremely stable to hydrolysis both in solution and in layers, and that thus a stable recording material containing these compounds can be produced. As described in the Preparation Examples, the acetals according to the invention are based on certain aldehydes, of which the following are particularly preferred as starting compounds:
2-, 3- and 4-hydroxybenzaldehyde
2,3-, 2,4-, 2,5- and 3,4-dihydroxybenzaldehyde,
2,3,4- and 3,4,5-trihydroxybenzaldehyde,
4-hydroxy-3-methyl-benzaldehyde,
2-hydroxy-4-methoxy-benzaldehyde,
2-hydroxy-5-methoxy-benzaldehyde,
3-hydroxy-4-methoxy-benzaldehyde,
4-hydroxy-3-methoxy-benzaldehyde,
4-hydroxy-3,5-dimethyl-benzaldehyde,
5-hydroxy-3,4-dimethoxy-benzaldehyde,
3-ethoxy-4-hydroxy-benzaldehyde,
2-hydroxy-5-nitro-benzaldehyde,
3-hydroxy-4-nitro-benzaldehyde,
4-hydroxy-3-nitro-benzaldehyde,
5-hydroxy-2-nitro-benzaldehyde, and
2-hydroxy-naphthalene-1-carbaldehyde These aldehydes are commercially available, while other hydroxyaldehydes suitable according to the invention as precursors can in general be prepared in a simple manner by the most diverse methods. A review of these is given in Houben-Weyl, Methoden der organischen Chemie [Methods of Organic Chemistry], vol. 7/1.

According to the invention, a positive-working radiation-sensitive mixture is also provided which comprises, a) a binder which is insoluble in water and soluble or at least swellable in aqueous alkaline solutions and b) a compound which generates a strong acid under the action of actinic radiation and which has at least one acid-cleavable C-O-C bond, wherein the compound (b) comprises a compound of the formula I described above.

The radiation-sensitive mixtures according to the invention, are distinguished by high sensitivities over a wide spectral range. They are very particularly suitable for irradiation with high-energy UV radiation, preferably with light of a wavelength from 190 to 350 nm. They show high thermal stability and make it possible to accurately reproduce even superfine structures of an original. No corrosive photolysis products are generated by the exposure, so that the mixture can also be used on sensitive substrate materials.

The acid-cleavable photolytic acid generators, (b) contained in the radiation-sensitive mixture according to the invention can be used singly or in combination with other acid-cleavable photolytic acid generators having the Formula I. Furthermore, combinations with other photolytic acid generators are also possible. Any known further acid generators can be used in admixture with compounds of Formula I. Even the onium salts mentioned at the outset, halogen compounds, especially trichloromethyltriazine-derivatives or trichloromethyloxadiazole derivatives, o-quinonediazidesulfochlorides or organometal/organo-halogen combinations are suitable. Overall, however, such combinations are not preferred since the disadvantages already mentioned in connection with the additional acid generators can under certain circumstances reappear in such radiation-sensitive mixtures.

The content of acid-cleavable photolytic acid generators of the formula I in the mixture according to the invention can be varied according to the intended use of the mixture and is in general between 2 and 60% by weight, preferably 5 to 50% by weight and particularly preferably 10 to 40% by weight, each relative to the total weight of solids in the mixture.

If desired, other acid-clearable compounds can be added to the mixtures according to the invention. Any known acid-cleavable compound can be used as the additional compounds. The following compound classes have proven suitable:

(1) compounds having at least one orthocarboxylic acid ester grouping and/or carboxylic acid amide-acetal grouping, the compounds also having a polymeric character and it being possible for the said groupings to occur as linking elements in the main chain or as substituents in side chains (see DE-A 2,610,842 and 2,928,636), (2) oligomeric or polymeric compounds with recurring acetal and/or ketal groupings in the main chain (see DE-A 2,306,248 and 2,718,254), (3) compounds having at least one enol ether grouping or N-acyliminocarbonate grouping (see EP-A 0,006,626 and 0,006,627), (4) cyclic acetals or ketals of β-ketoesters or β-ketoamides (see EP-A 0,202,196), (5) compounds having silyl ether groupings (see DE-A 3,544,165 and 3,601,264), (6) compounds having silylenol ether groupings (see DE-A 3,730,785 and 3,730,783), (7) monoacetals and monoketals, whose aldehyde or keto component respectively has a solubility of between 0.1 and 100 g/l in the developer (see DE-A 3,730,787), (8) ethers based on tertiary alcohols (see U.S. Pat. No. 4,603,101) and (9) carboxylic acid esters and carbonates of tertiary alcohols, allylic alcohols or benzylic alcohols [see U.S. Pat. No. 4,491,628 and J. M. Frechet et al., J. Imaging Sci. 30, 59–64 (1986) ].

Mixtures of any of the above acid-cleavable compounds can also be used. However, acid-cleavable compounds are preferably used which are classified under one of the above-mentioned types (1) to (9) and, amongst these, especially those which have an acid-cleavable C—O—C bond. Amongst these, those compounds are particularly preferred which belong to the types (1), (2), (7) and (9). Under type (2), the polymeric acetals are especially preferred and, of the acid-cleavable compounds of type (7), those whose aldehyde or ketone component has a boiling point above 150° C., preferably above 200° C. are preferred. Overall, however, mixtures of additional acid-cleavable compound with compound I are not preferred.

Preferably compound (b) or the combination of compounds (b) is present in a concentration from 2 to 60% by weight.

The radiation-sensitive mixture according to the invention also contains at least one polymeric binder which is insoluble in water but soluble or at least swellable in aqueous alkaline solutions. Any known binder or mixture of binders can be used which meet this description. The binder is distinguished in particular by being compatible with the other constituents of the radiation-sensitive mixture according to the invention and having the lowest possible characteristic absorption, i.e., high transparency, especially in the wavelength range from 190 to 350 nm.

Binders based solely on novolak condensation resins, which are generally used in combination with naphthoquinonediazides as the photoactive components, do not meet this requirement. Although novolak condensation resins show, after imagewise exposure, an increase in the solubility in aqueous alkaline developers in the exposed areas, their characteristic absorption is undesirably high in the region of the short wavelength desired for the irradiation.

Novalak condensation resins can, however, be used as binders when in a mixture with other resins of higher transparency. The mixing ratios here depend predominantly on the nature of the binder to be mixed with the novolak resin. Especially important factors are the degree of characteristic absorption of the binder in the said wavelength range, and also the miscibility with the other constituents of the radiation-sensitive mixture. In general, however, the binder of the radiation-sensitive mixture according to the invention preferably contains at most 30% by weight, especially at most 20% by weight, of a novolak condensation resin.

Suitable binders include homopolymers or copolymers of p-hydroxystyrene and homo and copolymers of alkyl derivatives thereof, for example of 3-methyl-4-hydroxystyrene, of 3,5-dimethyl-4-hydroxystyrene or of 2,3-dimethyl--4-hydroxystyrene. Also useful are homopolymers or copolymers of other vinylphenols, for example of 2- or 3-hydroxystyrene or of 4-methyl-3-hydroxystyrene, or the esters or amides of (meth)acrylic acid with phenols, for example pyrocatechol, resorcinol, hydroquinone, pyrogallol or aminophenols and the corresponding amides with aromatic amines. Polymerizable compounds such as styrene, methyl methacrylate, methyl acrylate or the like can be used as comonomers in the above polymers.

Mixtures having an increased plasma resistance are obtained when silicon-containing vinyl monomers, for example vinyltrimethylsilane or allyltrimethylsilane, are used in the preparation of copolymers of the above type. The transparency of these binders is generally higher in the region of interest, so that improved structuring is possible.

Homopolymers or copolymers of maleimide can also be used. These binders too show a high transparency in the wavelength range described. Here again, the comonomers preferably used are styrene, substituted styrenes, vinylphenols, vinyl ethers, vinyl esters, vinylsilyl compounds or (meth)acrylates.

Copolymers of styrene can also be used with comonomers which effect an increase in solubility in aqueous alkaline solutions. These include, for example, maleic anhydride, maleic acid half-esters or the like.

The said binders can be used alone or as mixtures with one another if this does not impair the optical quality of the radiation-sensitive mixture. However, binder mixtures are not preferred.

Any amount of binder can be used depending on the intended use of the mixture. The quantity of binder is in general 40 to 98% by weight, especially 50 to 95% by weight, preferably 60 to 90% by weight, relative to the total weight of the solids of the radiation-sensitive mixture.

The extinction of the binder or of the combination of binders (a) in the wavelength range of the sensitivity of compound (b) is preferably less than 0.5 $\mu m^{-1}$.

If appropriate, one or more of dyes, pigments, plasticizers, wetting agents and flow agents, and polyglycols and cellulose ethers, for example ethylcellulose, can be added to the radiation-sensitive mixtures according to the invention to improve special requirements, such as flexibility, adhesion and gloss.

Any substrate known in the art may be coated with the mixture according to the invention, and coated in any known manner. When a substrate is to be coated, the radiation-sensitive mixture according to the invention is expediently dissolved in a solvent or in a combination of solvents. Ethylene glycol, ethylene glycol monomethyl ether, ethylene glycol dimethyl ether, ethylene glycol monoethyl ether or propylene glycol monoalkyl ethers, (especially propylene glycol methyl ether), aliphatic esters (for example ethyl acetate, hydroxyethyl acetate, alkoxyethyl acetate, n-butyl acetate, propylene glycol alkyl etheracetate, especially propylene glycol methyl ether-acetate or amyl acetate), ethers (for example dioxane), ketones (for example methyl ethyl ketone, methyl isobutyl ketone, cyclopentanone and cyclohexanone), dimethylformamide, dimethylacetamide, hexamethylphosphoramide, N-methyl-pyrrolidone, butyrolactone, tetrahydrofuran and mixtures of the above are particularly suitable for this purpose. Glycol ethers, aliphatic esters and ketones are particularly preferred.

Ultimately, the choice of the solvents depends on the coating process used, on the desired layer thickness and on the drying conditions. The solvents must also be chemically neutral, i.e., they must not react irreversibly with the other layer components.

The solution prepared with the said solvents generally has a solids content from 5 to 60% by weight, preferably up to 50% by weight.

The invention also relates to a positive-working radiation-sensitive recording material which comprises a substrate and, preferably located thereon, a radiation-sensitive layer comprising a radiation-sensitive mixture according to the invention.

Possible substrates are all those materials of which capacitors, semiconductors, multi-layer printed circuits or integrated circuits are composed or from which these can be produced. Silicon substrates which can also be thermally oxidized and/or coated with aluminum and doped merit special mention. In addition, all other substrates usual in semiconductor technology are possible, such as silicon nitride, gallium arsenide and indium phosphide. Moreover, the substrates known from liquid crystal display manufacture are possible, such as, for example, glass and indium-tin oxide and also metal plates and foils, for example foils of aluminum, copper and zinc, bimetal foils and trimetal foils, and also electrically non-conductive foils on which metals have been vapordeposited, and paper. These substrates can have been thermally pretreated, superficially roughened, incipiently etched or pretreated with chemicals to improve desired properties, for example to enhance the hydrophilic character.

To impart better cohesion and/or better adhesion of the radiation-sensitive layer to the substrate surface, the layer can contain an adhesion promoter. In the case of silicon or silica substrates, adhesion promoters of the aminosilane type such as, for example, 3-aminopropyl-triethoxysilane or hexamethyldisilazane, can be used for this purpose. Also, a layer containing an adhesion promoter can be coated onto the substrate prior to applying the radiation sensitive mixture.

Suitable supports for the production of photomechanical recording layers, such as printing forms for letterpress printing, planographic printing, screen printing and flexographic printing, are, in particular, aluminum plates, which may have been anodically oxidized, grained and/or silicated before hand, zinc and steel plates which may be chromium-plated, and plastic films and paper.

The recording material according to the invention is exposed imagewise to actinic radiation. Any source of actinic radiation can be used. Suitable radiation sources are especially metal halide lamps, carbon arc lamps, xenon lamps and mercury vapor lamps. Likewise, exposure can be carried out with high-energy radiation such as laser radiation, electron beams or X-rays. However, lamps which can emit light of a wavelength from 190 to 260 nm, i.e., especially xenon lamps and mercury vapor lamps, are particularly preferred. Furthermore, laser light sources can also be used, for example, excimer lasers, especially KrF or ArF lasers, which emit at 248 and 193 nm respectively. The radiation sources must show adequate emission in the said wavelength ranges.

The thickness of the light-sensitive layer depends on the intended use and hence can vary accordingly. In general it is between 0.1 and 100 μm, preferably between 1 and 10 μm.

The invention also relates to a process for producing a radiation-sensitive recording material. The radiation-sensitive mixture can be applied to the substrate by any known process such as spraying, flow-coating, rolling, whirler-coating and dip-coating. The solvent is then removed by evaporation, so that the radiation-sensitive layer remains on the surface of the substrate. The removal of the solvent can be promoted by heating the layer to temperatures of up to 150° C. The mixture can, however, be first applied in the above-mentioned way to a temporary support from which it is transferred under pressure and at an elevated temperature to the final support material. The materials used as temporary support can in principle be all those which are also suitable as support materials. Subsequently, the layer is irradiated imagewise and heated to intensify the cleavage reaction. The layer is then treated with a developer solution which dissolves and removes the irradiated areas of the layer, so that an image of the original used in the imagewise irradiation remains on the substrate surface.

Any developer known in the art can be used. Suitable developers are especially aqueous solutions which contain silicates, metasilicates, hydroxides, hydrogen phosphates and dihydrogen phosphates, carbonates or hydrogen carbonates of alkali metal ions, alkaline earth metal ions and/or ammonium ions, and also ammonia and the like. Metal ion-free developers are described in U.S. Pat. No. 4,729,941, EP-A 0,062,733, U.S. Pat. Nos. 4,628,023, 4,141,733, EP-A 0,097,282 and EP-A 0,023,758. The content of these substances in the developer solution is in general 0.1 to 15% by weight, preferably 0.5 to 5% by weight, relative to the weight of the developer solution. Preferably, metal ion-free developers are used. Small quantities of a wetting agent can have been added to the developers, in order to facilitate the detachment of the soluble areas of the layer.

The developed layer structures can be post-hardened. This is effected in any known manner, in general by heating on a hotplate up to a temperature below the flow temperature and subsequently exposuring the whole area to the UV light from a xenon-mercury vapor lamp (range from 200 to 250 nm). As a result of the post-hardening, the image structures are cross-linked, so that in general they have a flow resistance up to temperatures of more than 200° C. The posthardening can also be effected without a temperature increase solely by irradiation with high-energy UV light.

The radiation-sensitive mixture according to the invention may be used in the production of integrated circuits or of discrete electronic components by lithographic processes because they have a high light sensitivity, particularly on irradiation with light of a wavelength of between 190 and 350 nm. Since the mixtures bleach very well on exposure, finer structures can be achieved than is possible with the known mixtures. The developed resist layer here serves as a mask for the subsequent process steps. Examples of such steps are the etching of the layer support, the implantation of ions in the layer support or the precipitation of metals or other materials on the layer support.

Examples 1 to 10 which follow demonstrate the suitability of the mixture according to the invention for recording materials in microlithography using high-energy radiation. The superiority of the mixtures according to the invention over the state of the art is demonstrated by reference to Comparison Examples 11 and 12.

In the examples, the quantities are stated as parts by weight (p.b.w.). Unless otherwise stated, percentage figures and quantitative ratios are to be understood as being in weight units.

Example 1

A coating solution was prepared from
6.0 p.b.w. of a styrene/p-hydroxystyrene copolymer (molar ratio 30:70) having a mean molecular weight of 27,000,
1.5 p.b.w. of a cresol/formaldehyde novolak having a softening range from 105° to 120° C. and
2.0 p.b.w. of Compound 1 in
42 p.b.w. of propylene glycol monomethyl ether acetate.

The solution was filtered through a filter of 0.2 μm pore diameter and whirler-coated at 3,300 rpm onto a wafer treated with an adhesion promoter (hexamethyldisilazane). After drying for 1 minute at 100° C. on a hotplate, a layer thickness of 1.05 μm was obtained.

The recording material was exposed imagewise under an original to the UV radiation of a xenon-mercury vapor lamp (using a filter with a transmission from 240 to 260 nm) with an energy of 78 mJ/cm$^2$ and stored for about 30 minutes at room temperature before development.

The recording material was developed using a 0.3N alkaline developer of the following composition:
5.3 p.b.w. of sodium metasilicate×9 H$_2$O,
3.4 p.b.w. of trisodium phosphate×12 H$_2$O,
0.3 p.b.w. of sodium dihydrogen phosphate and
191 p.b.w. of deionized water.

After a developing time of 60 seconds, this gave a defect-free positive image of the mask with steep resist flanks, and structures of <0.6 μm were resolved in true detail. An examination of the flanks of the resist profiles by means of scanning electron microscopy proved that these were aligned virtually perpendicular to the substrate surface.

Example 2

A coating solution was prepared from
7.5 p.b.w. of a styrene/p-hydroxystyrene copolymer (molar ratio 20:80) having a mean molecular weight of 32,000 and
2.0 p.b.w. of Compound 2 in
42 p.b.w. of propylene glycol monomethyl etheracetate.

The solution was filtered through a filter of 0.2 μm pore diameter and whirler-coated at 3,300 rpm onto a wafer treated with an adhesion promoter (hexamethyldisilazane). After drying for 1 minute at 100° C. on a hotplate, a layer thickness of 1.12 μm was obtained.

The recording material was exposed imagewise under an original to the UV radiation of a xenon-mercury vapor lamp at 240 to 260 nm with an energy of 82 mJ/cm$^2$, stored for about 30 minutes at room temperature and then processed using the developer described in Example 1.

After a developing time of 60 seconds, this gave a defect-free image of the mask with high flank stability Here again, structures of <0.6 μm were resolved in true detail.

Example 3

A wafer produced according to Example 1 was irradiated under an original with KrF-excimer laser with radiation of 248 nm wavelength and an energy of 100 mJ/cm$^2$. After development, an image true to the original was obtained.

Example 4

A coating solution was prepared from
7.5 p.b.w. of the copolymer indicated in Example 2 and
2.0 p.b.w. Compound 3 in
42 p.b.w. of propylene glycol monomethyl etheracetate.

The solution was filtered through a filter of 0.2 μm pore diameter and whirler-coated at 3,300 rpm onto two wafers in total, treated with an adhesion promoter (hexamethyldisilazane). After drying for 1 minute at 100° C. on a hotplate, a layer thickness of 1.04 μm was obtained in both cases.

One of the coated wafers was exposed imagewise under an original to the Lr Vradiation of an xenon-mercury vapor lamp at 240 to 260 nm with an energy of 60 mJ/cm$^2$, heated for 75 seconds to 100° C. and then processed using a developer which was composed of 3% tetramethylammonium hydroxide and 97% deionized water.

After a developing time of 60 seconds, this gave a defect-free image of the mask with high flank stability. Here again, structures of <0.6 μm were resolved in true detail.

The second wafer was exposed, heat-treated and developed as described above after 14 days. Virtually the same results as described above were obtained. This means that the mixture applied in the dried form to a substrate has excellent stability.

Example 5

A coating solution was prepared from
7.5 p.b.w. of a 3-methyl-4-hydroxystyrene homopolymer having a mean molecular weight of 25,000 and
2.0 p.b.w. of Compound 1 in
42 p.b.w. of propylene glycol monomethyl etheracetate.

The solution was filtered through a filter of 0.2 μm pore diameter and divided into two equal parts. One part was whirler-coated at 3,300 rpm onto a wafer treated with an adhesion promoter (hexamethyldisilazane). After drying for 1 minute at 100° C., a layer thickness of 1.04 μm was obtained.

The recording material was exposed imagewise under an original to the radiation of a xenon-mercury vapor lamp at 240 to 260 nm with an energy of 80 mJ/cm$^2$, heated for 75 seconds at 100° C. and then processed using the developer described in Example 4.

After a developing time of 60 seconds, a defect-free image of the mask with high flank stability was obtained. Here again, structures of <0.6 μm were resolved in true detail.

The second part was subjected to the same procedure after storage for 20 weeks in the refrigerator. Identical results were obtained, which shows that the mixture has an extraordinarily high stability in solution.

Example 6

A coating solution was prepared from
7.5 p.b.w. of a 3,5-dimethyl-4-hydroxystyrene/4-hydroxystyrene copolymer (molar ratio 20:80) having a mean molecular weight of 25,000 and
2.0 p.b.w. of Compound 4 in
42 p.b.w. of propylene glycol monomethyl etheracetate.

The solution was filtered through a filter of 0.2 μm pore diameter and whirler-coated at 3,300 rpm onto a wafer treated with an adhesion promoter (hexamethyldisilazane). After drying at 100° C. for 1 minute, a layer thickness of 1.08 μm was obtained.

The recording material was exposed imagewise under an original to the UV radiation of a xenon-mercury vapor lamp at 240 to 260 nm with an energy of 72 mJ/cm², heated for 75 seconds at 100° C. and then processed using the developer described in Example 1.

After a developing time of 60 seconds, a defect-free image of the mask with high flank stability was obtained. Here again, structures of <0.6 μm were resolved in true detail.

Example 7

Example 4 was repeated twice, with the modification that, instead of 60 seconds at 100° C., drying was carried out for 90 seconds at 90° C. and for 60 seconds at 100° C., respectively. In both cases, the results were virtually identical and were the same as those described in Example 4. This means that the recording material according to the invention has a wide processing latitude.

Example 8

A coating solution was prepared from 7.5 p.b.w. of a styrene/maleimide copolymer (molar ratio 1:1) having a softening range from 165° to 180° C. and 2.0 p.b.w. of Compound 4 in 42 p.b.w. of cyclohexanone.

The solution was filtered through a filter of 0.2 μm pore diameter and whirler-coated at 3,400 rpm onto a wafer treated with an adhesion promoter (hexamethyldisilazane). After drying for 1 minute at 100° C., a layer thickness of 0.98 μm was obtained.

The recording material was exposed imagewise under an original to the radiation of a xenon-mercury vapor lamp at 240 to 260 nm with an energy of 89 mJ/cm².

The recording material was developed using a 0.02 N aqueous solution of tetramethylammonium hydroxide and, the exposed areas were detached without residues within 60 seconds.

Again, a defect-free image of the mask with steep resist flanks was obtained. The loss in the dark was less than 20 nm; even structures smaller than 0.6 μm were resolved in true detail.

Example 9

A coating solution was prepared from 7.5 p.b.w. of the copolymer indicated in Example 8 and 2.0 p.b.w. of Compound 11 in 42 p.b.w. of cyclohexanone.

The solution was filtered through a filter of 0.2 μm pore diameter and whirler-coated at 3,500 rpm onto a wafer treated with an adhesion promoter (hexamethyldisilazane). After drying for 1 minute at 100° C., a layer thickness of 1.04 μm was obtained.

The recording material was exposed imagewise under an original to the radiation of a xenon-mercury vapor lamp at 240 to 260 nm with an energy of 67 mJ/cm².

The recording material was developed using a 0.02N aqueous solution of tetramethylammonium hydroxide. The exposed areas were detached without residues within 60 seconds, and an image of the original in true detail was obtained. The edge steepness of the image was excellent.

Example 10

A coating solution was prepared from 7.5 p.b.w. of the copolymer described in Example 2 and 2.0 p.b.w. of Compound 23 in 42 p.b.w. of propylene glycol monomethyl etheracetate.

The solution was filtered through a filter of 0.2 μm pore diameter and whirler-coated at 3,100 rpm onto a wafer treated with an adhesion promoter (hexamethyldisilazane). After drying for 1 minute at 100° C., a layer thickness of 1.07 μm was obtained.

The recording material was exposed imagewise under an original to the radiation of a xenon-mercury vapor lamp at 240 to 260 nm with an energy of 75 mJ/cm². The recording material was developed using a 0.27N aqueous tetramethylammonium hydroxide solution. The exposed areas were detached without residues within 60 seconds, and an image of the original in true detail being obtained. Lines and gaps down to 0.5 μm were reproduced true to the mask. It was found that the solution of the material as produced still gave reproducible lithographic results identical to the first tests even after storage in the dark for 6 weeks.

Examples 11 and 12 (Comparison Examples)

The resist formulation of Example 2 was modified in such a way that in each case 0.2 p.b.w. of the compounds, known as acid generators, triphenylsulfonium hexafluorophosphate (Example 11) and 2-nitrobenzyl tosylate (Example 12) were added to the mixture. After coating and drying, it was found that the formulation of Example 11 is about 10% more sensitive than the mixture according to the invention of Example 2 to KrF-excimer laser light of 248 nm wavelength under identical process conditions, while the sensitivity of the formulation of Example 12 does not differ from that of Example 2.

When the onium salt (Example 11) was used, however, structures having a so-called "coating foot" were obtained, i.e., residues of the resist adhered to the substrate in the exposed areas. When the tosyl ester was used (Example 12), surface crosslinkings were visible which partially overlapped the bared substrate surfaces. In both cases, acceptable structuring was thus not obtainable.

What is claimed is:

1. A positive-working radiation-sensitive mixture which comprises:
    a) a polymeric binder which is insoluble in water and soluble or at least swellable in aqueous alkaline solutions, and
    b) an oligomer having repeating units of the formula

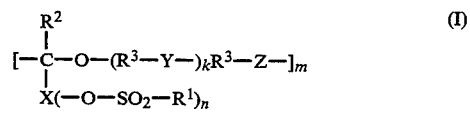

in which

R¹ is an alkyl, halalkyl or aryl radical,

R² is a hydrogen atom, an alkyl, alkenyl or aryl radical or the group $R^1-SO_2-O)_nX-$, R³ is a cycloalkylenedialkyl, cycloalkenylenedialkyl, arylenedialkyl, heteroarylenedialkyl, alkylene, alkenylene, alkynylene, cycloalkylene or arylene group, X is an alkylene, cycloalkylene or arylene group if n is 1, or a (n+1)-valent radical of an alkene, cycloalkene, or arene if n is 2 or 3.

Y is O, S, CO, CO—O, $SO_2$, $NR^4$, CO—NH, O—CO—$NR^5$, NH—CO—$NR^5$—CO—O,

Z is O, CO—$NR^6$, O—CO—$NR^5$ or NH—CO—$NR^6$, $R^4$ is an acyl radical, $R^5$ is a hydrogen atom or an alkyl-, cycloalkyl, alkenyl, alkynyl or aryl radical, $R^6$ is an alkyl, cycloalkyl, alkenyl, alkynyl or aryl radical, k is 0, 1, 2, 4 or 4, m is an integer greater than 1 and n is 1, 2 or 3, where $R^3$ and Y in recurring groupings ($R^3$—Y—) can have identical or different definitions.

2. A radiation-sensitive mixture as claimed in claim 1, wherein $R^1$ is an alkyl, highly fluorinated alkyl or perfluoro-alkyl radical, each having 1 to 6 carbon atoms or an aryl radical having 6 to 12 carbon atoms, wherein the aryl radical is optionally substituted with one or more of halogen atoms, nitro groups, cyano groups, or alkyl or alkoxy groups having 1 to 3 carbon atoms.

3. A radiation-sensitive mixture as claimed in claim 1, wherein $R^2$ is a hydrogen atom.

4. A radiation-sensitive mixture as claimed in claim 1, wherein $R^2$ is the group ($R^1$—$SO_2$—O—$)_n$X—.

5. A radiation-sensitive mixture as claimed in claim 1, wherein X is an alkylene or cycloalkylene group having 2 to 10 carbon atoms or an arylene group having 6 to 12 carbon atoms.

6. A radiation-sensitive mixture as claimed in claim 1, wherein $R^4$ is an aroyl radical.

7. A radiation-sensitive mixture as claimed in claim 1, wherein m is greater than 3.

8. A radiation-sensitive mixture as claimed in claim 1, wherein m is between 4 and 40.

9. A radiation-sensitive mixture as claimed in claim 1, wherein said oligomer (b) is sensitive to light of a wavelength from 190 to 350 nm.

10. A radiation-sensitive mixture as claimed in claim 1, which contains (b) in a concentration from 2 to 60% by weight, based on the total weight of solids present in the mixture.

11. A radiation-sensitive mixture as claimed in claim 1, wherein (a) has an extinction of less than 0.5 $\mu m^{-1}$ in the wavelength region of the sensitivity of (b).

12. A radiation-sensitive mixture as claimed in claim 11, wherein (a) comprises a polymer having phenolic hydroxy groups.

13. A radiation-sensitive mixture as claimed in claim 1, which contains (a) in a concentration from 40 to 98% by weight, based on the total weight of solids in the mixture.

14. A radiation-sensitive mixture as claimed in claim 1, wherein said (a) comprises at most 30% by weight of a novolak condensation resin.

15. A radiation-sensitive recording material comprising a support and a radiation-sensitive layer, wherein the layer is comprised of a radiation-sensitive mixture as claimed in claim 1.

16. A method of producing a recording material as claimed in claim 15 which comprises applying said radiation-sensitive layer to said support.

17. A method as claimed in claim 16, comprising dissolving said mixture in a solvent to form a solution, applying the resultant solution to said support, and removing said solvent.

18. A method as claimed in claim 16, which comprises first applying said radiation-sensitive layer to a temporary support, and then applying said support to said radiation-sensitive layer, and then optionally removing said temporary support.

19. A radiation-sensitive mixture as claimed in claim 1, wherein the polymeric binder comprises a homopolymer or copolymer of p-hydroxystyrene or of an alkyl derivative thereof.

20. A coating solution comprising a solvent and a mixture as claimed in claim 1.

* * * * *

UNITED STATES PATENT AND TRADEMARK OFFICE
CERTIFICATE OF CORRECTION

PATENT NO. : 5,346,806
DATED : September 13, 1994
INVENTOR(S) : PAWLOWSKI et al.

It is certified that error appears in the above-indentified patent and that said Letters Patent is hereby corrected as shown below:

Column 34, line 66, Claim 1, contains a typographical error wherein "$R^1$" should read --($R^1$--.

Column 35, line 16, Claim 1, contains a typographical error wherein "k is 0,1,2,4, or 4" should read --k is 0,1,2,3, or 4--.

Signed and Sealed this

Twenty-eight Day of March, 1995

*Attest:*

BRUCE LEHMAN

*Attesting Officer*   *Commissioner of Patents and Trademarks*